(12) United States Patent
Belmant et al.

(10) Patent No.: US 7,101,711 B1
(45) Date of Patent: Sep. 5, 2006

(54) PHOSPHOEPOXIDES, METHOD FOR MAKING SAME AND USES

(75) Inventors: Christian Belmant, Blagnac (FR); Jean-Jacques Fournie, Corronsac (FR); Marc Bonneville, Vertou (FR); Marie-Alix Peyrat, Saint-Sebastien sur Loire (FR)

(73) Assignee: Institut National de la Santa et de la Recherche Medicale, Paris (FR)

( * ) Notice: Subject to any disclaimer, the term of this patent is extended or adjusted under 35 U.S.C. 154(b) by 0 days.

(21) Appl. No.: 09/786,055

(22) PCT Filed: Aug. 27, 1999

(86) PCT No.: PCT/FR99/02057

§ 371 (c)(1),
(2), (4) Date: Mar. 1, 2001

(87) PCT Pub. No.: WO00/12519

PCT Pub. Date: Mar. 9, 2000

(30) Foreign Application Priority Data

Sep. 1, 1998 (FR) .................................. 98 10914

(51) Int. Cl.
C12N 5/02 (2006.01)
C12N 5/08 (2006.01)
A61K 31/66 (2006.01)

(52) U.S. Cl. ...................... 435/384; 435/386; 435/325; 435/372.3; 514/102; 514/106; 558/152; 558/156

(58) Field of Classification Search .................... 514/1, 514/75, 99, 106, 124, 129, 44
See application file for complete search history.

(56) References Cited

U.S. PATENT DOCUMENTS 5,639,653 A 6/1997 Bloom et al.

FOREIGN PATENT DOCUMENTS

WO    WO 95/20673    8/1995

OTHER PUBLICATIONS

Yamaguchi et al (J. Immunol. Met. 205(1): 19-28, Jun. 23, 1997.*
Janssen et al (J. Immunol. 146(1): 35-39, Jan. 1, 1991).*
Lopez et al (Blood 96(12): 3827-3837, Dec. 1, 2000).*
Muehlbacher et al (Biochemistry 27:7315-7328, 1988).*
Y. Tanaka et al., Natural and Synthetic Non-Peptide Anti-Gens Recognized by Human γδ T Cells, *Nature*, vol. 375, May 11, 1995, pp. 155-158.
D. Wesch et al., Comparative Analysis of αβ and γδ T Cell Activation by *Mycobacterium tuberculosis* and Isopentenyl Pyrophosphate, *Euro. J. Immunol.*, vol. 27, No. 4, 1997, pp. 952-956.
M. R. Bürk et al., Human Vγ9-Vδ2 Cells are Stimulated in a Cross-Reactive Fashion by a Variety of Phosphorylated Metalbolites, *Euro. J. Immunol.*, 1995, vol. 25, No. 7, pp. 2052-2058.
B. Schoel et al., Phosphate is Essential for Stimulation of Vγ9Vδ2 T Lymphocytes By Mycobacterial Low Molecular Weight Ligand, *Eur. J. Immunol.*, 1994, vol. 24, No. 8, pp. 1886-1892.
M. Muehlbacher et al., Isopentenyl-Diphosphate Isomerase: Inactivation of the Enzyme with Active-Site-Directed Irreversible Inhibitors and Transition-State Analogues, *Biochemistry*, vol. 27, 1988, pp. 7315-7328.
F. Poccia et al., γδ T Cell Activation or Anergy During Infections: The Role of Non Peptidic TCR Ligands and HLA Class I Molecules, *Journal of Leukcyte Biology*, vol. 62, Sep. 1997, pp. 1-5.
P. Constant et al., The Antituberculous *Mycobacterium bovis* BCG Vaccine is an Attenuated Mycobacterial Producer of Phosphorylated Nonpeptidic Antigens for Human γδ T Cells, *Infection and Immunity*, vol. 63, No. 12, Dec. 1995, pp. 4628-4633.
C. Behr et al., *Plasmodium Falciparum* Stimuli for Human γδ T Cells are Related to Phosphorylated Antigens of Mycobacteria, *Infection and Immunity*, vol. 64, No. 8, pp. 2892-2896.
F. Poccia et al., CD94/NKG2 Inhibitory Receptor Complex Modulates Both Anti-Viral and Anti-Tumoral Responses of Polyclonal Phosphoantigen-Reactive Vγ9Vδ2 T Lymphocytes[1], *The American association of Immunologies*, 1997, pp. 6009-6017.
Fournie et al., Stimulation of γδ T Cells By Phosphoantigens, *66th Forum in Immunology*, May 1996, pp. 338-346.
P. Constant et al., Stimulation of Human γδ T Cells By Nonpeptidic Mycobacterial Ligands, *Science*, vol. 264, Apr. 8, 1994, pp. 267-270.
Poquet et al., A Novel Nucleotide-Containing Antigen for Human Blood γδT Lymphocytes, *Eur. J. Immunol.*, vol. 26, 1996, pp. 2344-2349.
Y. Poquet et al., High-PH Anion-Exchange Chromatographic Analysis of Phosphorylated Compounds: Application to Isolation and Characterization of Nonpeptide Mycobacterial Antigens, *Analytical Biochemistry*, vol. 243, 1996, pp. 119-126.
V.J. Davisson et al., Phosphorylation of Isoprenoid Alcohols, *American Chemical Society, J. Org. Chem.*, vol. 51, 1986, pp. 4768-4779.
V.J. Davisson et al., Synthesis of Allylic and Momoallylic Isoprenoid Phyrophosphates, *J. American Chemical Society*, vol. 97, No. 7152, 1975 pp. 130-144.
D.G. Knorre et al., General Method for the Synthesis of ATP Gamma-Derivatives, *FEBS Letters*, vol. 70, No. 1, Nov. 1976, pp. 105-108.

* cited by examiner

*Primary Examiner*—Richard Schnizer
(74) *Attorney, Agent, or Firm*—Saliwanchik, Lloyd & Saliwanchik (57) ABSTRACT

The invention provides compounds comprising at least one phosphoepoxide group of the formula:

$$R1-\underset{\underset{CH_2}{\diagup\diagdown}}{C}-(CH_2)_n-O-\underset{\underset{Cat^+}{O^-}}{\overset{\overset{O}{\|}}{P}}-O-\underset{\underset{Cat^+}{O^-}}{\overset{\overset{O}{\|}}{P}}-O- \quad (1)$$

where R1 is selected from among —$CH_3$ and —$CH_2$—$CH_3$,
Cat+ is an organic or inorganic cation,
n is an integer between 2 and 20,
processes for the production thereof and uses thereof, in particular therapeutic uses and for activating primate Tγ9δ2 lymphocytes.

17 Claims, 2 Drawing Sheets

PHOSPHOEPOXIDES, METHOD FOR MAKING SAME AND USES

BACKGROUND

This invention relates to novel phosphoepoxides, to the process for the production thereof and to the use thereof for stimulating Tγ9δ2 lymphocytes bearing TCR receptors with Vγ9 and Vδ2 variable regions.

In healthy individuals, the Tγδ lymphocytes of primates (humans, monkeys) present in the peripheral bloodstream usually constitute from 1 to 5% of the lymphocytes in the blood and play a role in the immune system. It has been demonstrated that they recognize their antigenic ligands by direct interaction with the antigen without presentation by molecules of the MHC by a presenting cell. Tγ9δ2 lymphocytes (sometimes also known as Tγ2δ2 lymphocytes) are Tγδ lymphocytes bearing TCR receptors with Vγ9 and Vδ2 variable regions. They constitute the majority of Tγδ lymphocytes in human blood.

When activated, Tγδ lymphocytes exercise a strong cytotoxic activity which is unrestrained by the MHC and is particularly effective in killing various types of cells, in particular pathogenic cells. These may be cells infected by viruses ("γδ T cell activation or anergy during infections: the role of nonpeptidic TCR ligands and HLA class I molecules" Fabrizio POCCIA et al, Journal of Leukocyte Biology, 62, 1997, p. 1–5), or by other intracellular parasites, such as mycobacteria ("The antituberculous *Mycobacterium bovis* BCG Vaccine is an attenuated Mycobacterial producer of phosphorylated nonpeptidic Antigens for human γδ T cells" Patricia CONSTANT et al, Infection and Immunity, vol. 63, no. 12, December 1995, p. 4628–4633); or by protozoans ("*Plasmodium falciparum* stimuli for human γδ T Cells are related to phosphorylated Antigens of mycobacteria" Charlotte BEHR et al, Infection and Immunity, Vol. 64, no. 8, 1996, p. 2892–2896). They may also be cancer cells ("CD94/NKG2 inhibitory receptor complex modulates both antiviral and antitumoral responses of polyclonal phosphoantigen-reactive Vγ9 Vδ2 T lymphocytes" Fabrizio POCCIA et al, Journal of Immunology, 159, p. 6009–6015; "Stimulation of γδ T cells by phosphoantigens" Jean-Jacques FOURNIE, Marc BONNEVILLE, Res. Immunol., 66$^{th}$ FORUM IN IMMUNOLOGY, 147, p. 338–347).

It has been demonstrated that, in the event of a mycobacterial infection, human Tγ9δ2 lymphocytes react to four natural, nonpeptidic molecules of a phosphorylated structure, known as phosphoantigens, which exhibit stimulation activity at a concentration of 1 to 5 nM (nanomolar) (WO-95/20673 and "Stimulation of human γ δ T cells by nonpeptidic Mycobacterial ligands" Patricia CONSTANT et al, Science, 264, p. 267–270).

These natural antigens have not been completely identified. Certain authors have erroneously presented them as alkene derivatives of pyrophosphate, in particular isopentenyl pyrophosphate IPP (U.S. Pat. No. 5,639,653 and "Natural and Synthetic nonpeptide antigens recognized by human γδ T cells", Yoshimasa TANAKA et al, Nature, 375, 1995, p. 155–158). It has nonetheless now been demonstrated that none of these prenyl pyrophosphates is active at a concentration of nanomolar magnitude. The best results which have been obtained have been unable to demonstrate activity at below 3 μM for IPP and below 0.3 μM for dimethylallyl-UTP and 3-methyl-2-hexene pyrophosphate. The minimum active concentration of these compounds is thus, at best, of the order to 100 times higher than that of natural phosphoantigens.

With regard to IPP, it should in particular be noted that the most recent of the above-stated publications make the mistake of deducing the structure of the isopentenyl radical solely on the basis of mass spectrometry and the detection of a certain level of bioactivity. Indeed, apart from the fact that the compound analyzed in these publications was not purified and that a mass spectrum cannot identify uncharged species, it may be demonstrated that there are in fact several thousand different chemical structures which may have the same molecular weight and be a substituent of pyrophosphate in these molecules.

The fact that the minimum active concentration for IPP is much higher (some 1000 times higher) and that the intensity of the Tγ9δ2 lymphocyte responses obtained is much weaker than that for natural phosphoantigens demonstrates that IPP is not one of these natural phosphoantigens ("A novel nucleotide-containing antigen for human blood γδ T lymphocytes", Y. Poquet et al, Eur. J. Immunol. 1996, 26, p. 2344–2349). This is moreover confirmed by numerous other observations: IPP is not found in sufficient concentration in mycobacterial extracts which stimulate Tγ9δ2 lymphocytes; according to "High pH anion exchange chromatographic analysis of phosphorylated compounds: application to isolation and characterization of non peptide mycobacterial antigens", Y. Poquet et al, Anal. Biochem. 243 no. 1, 1996, p. 119–126, IPP does not have the same chromatographic (HPAEC) characteristics as natural phosphoantigens; IPP and other natural isoprenoids are produced by all living cells, but these do not stimulate Tγ9δ2 lymphocytes.

Moreover, it is known that substances having bioactivity of the order of or greater than 1 μM are only rarely compatible with the economic constraints of operation on an industrial scale. The synthetic phosphoantigens which have hitherto been proposed thus cannot be processed on an industrial scale under acceptable economic conditions.

Natural phosphoantigens, on the other hand, may only be produced in very small quantities (WO 95/20673) and, since their precise chemical structure has still not yet been established, they cannot be synthesized. Economic industrial scale processing is thus likewise out of the question, despite their demonstrated great therapeutic worth.

SUMMARY OF THE INVENTION

The object of the invention is accordingly to provide novel chemical compounds which activate Tγ9δ2 lymphocytes at a minimum activation concentration of below 100 nM, in particular of the order of 10 nM.

A further object of the invention is to provide compounds which may be linked to a large number of organic groups, in particular to natural or synthetic peptide groups, so as to permit multifunctional compounds to be obtained.

A further object of the invention is to provide a process for the production of the compounds according to the invention.

A further object of the invention is to suggest uses according to the invention as Tγ9δ2 lymphocyte activators and in particular therapeutic uses of the compounds according to the invention.

A further object of the invention is to provide such compounds which may be synthesized simply, quantitatively and at low cost, i.e. in a manner compatible with the economic constraints of production on an industrial scale.

A further object of the invention is to provide an advantageous synthetic pathway for these compounds.

A further object of the invention is to provide a process for the production of the compounds according to the invention.

A further object of the invention is to suggest uses for the compounds according to the invention as a Tγ9δ2 lymphocyte activator and in particular therapeutic uses of the compounds according to the invention.

DETAILED DESCRIPTION

The invention accordingly provides compounds comprising at least one phosphoepoxide group of the formula:

(1)

where R1 is selected from among —CH$_3$ and —CH$_2$—CH$_3$,

Cat$^+$ represents one or more organic or inorganic cation(s) (including the proton), which may be identical or different in the same compound, and n is an integer between 2 and 20.

A compound according to the invention may in particular comprise one or more epoxide group(s) selected from among the esters of the following groups (IUPAC nomenclature) or among the compounds formed from these groups: 3,4-epoxy-3-methyl-1-butyl diphosphate; 3,4-epoxy-3-ethyl-1-butyl diphosphate; 4,5-epoxy-4-methyl-1-pentyl diphosphate; 4,5-epoxy-4-ethyl-1-pentyl diphosphate; 5,6-epoxy-5-methyl-1-hexyl diphosphate; 5,6-epoxy-5-ethyl-1-hexyl diphosphate; 6,7-epoxy-6-methyl-1-heptyl diphosphate; 6,7-epoxy-6-ethyl-1-heptyl diphosphate; 7,8-epoxy-7-methyl-1-octyl diphosphate; 7,8-epoxy-7-ethyl-1-octyl diphosphate; 8,9-epoxy-8-methyl-1-nonyl diphosphate; 8,9-epoxy-8-ethyl-1-nonyl diphosphate; 9,10-epoxy-9-methyl-1-decyl diphosphate; 9,10-epoxy-9-ethyl-1-decyl diphosphate; 10,11-epoxy-10-methyl-1-undecyl diphosphate; 10,11-epoxy-10-ethyl-1-undecyl diphosphate; 11,12-epoxy-11-methyl-1-dodecyl-diphosphate; 11,12-epoxy-11-ethyl-1-dodecyl diphosphate; 12,13-epoxy-12-methyl-1-tridecyl diphosphate; 12,13-epoxy-12-ethyl-1-tridecyl diphosphate; 13,14-epoxy-13-methyl-1-tetradecyl diphosphate; 13,14-epoxy-13-ethyl-1-tetradecyl diphosphate; 14,15-epoxy-14-methyl-1-pentadecyl diphosphate; 14,15-epoxy-14-ethyl-1-pentadecyl diphosphate; 15,16-epoxy-15-methyl-1-hexadecyl diphosphate; 15,16-epoxy-15-methyl-1-hexadecyl diphosphate; 16,17-epoxy-16-methyl-1-heptadecyl-diphosphate; 16,17-epoxy-16-ethyl-1-heptadecyl diphosphate; 17,18-epoxy-17-methyl-1-octadecyl diphosphate; 17,18-epoxy-17-ethyl-1-octadecyl diphosphate; 18,19-epoxy-18-methyl-1-nonadecyl diphosphate; 18,19-epoxy-18-ethyl-1-nonadecyl diphosphate; 19,20-epoxy-1 g-methyl-1-eicosyl diphosphate; 19,20-epoxy-19-ethyl-1-eicosyl diphosphate; 20,21-epoxy-20-methyl-1-heneicosyl diphosphate; 20,21-epoxy-20-ethyl-1-heneicosyl diphosphate; 21,22-epoxy-21-methyl-1-docosyl diphosphate; 21,22-epoxy-21-methyl-1-docosyl diphosphate.

The invention also in particular relates to the novel phosphoepoxides of the following formula:

(2)

for the use thereof as therapeutically active substances. It should be noted that the publication by M. MUEHLBACHER et al, "Isopentenyl-diphosphate isomerase: inactivation of the enzyme with active-site-directed irreversible inhibitors and transition-state analogs", Biochemistry, vol. 27, no. 19, p. 7315–7328 (1988) has already described a compound according to the formula (2) in which R1 is CH3 and n=2, as well as the in vitro action thereof as an enzyme inhibitor on isopentenyl pyrophosphate isomerase purified from the mould *Claviceps purpurea*. Said document discloses no therapeutic use of this compound.

The invention accordingly also provides novel compounds comprising at least one phosphoepoxide group of the formula:

(3)

Among the novel compounds according to the invention of the formula (3) phosphoepoxide compounds which may be mentioned are those of the formula:

(4)

and the phosphoepoxide compounds of the formula:

(5)

where R2 is an organic or inorganic substituent selected from among the group comprising:

substituents which do not prevent formation of the halohydrin function starting from the alkene function and halogen $X_2$ in the presence of water;
  and substituents for which there is an R2-O—Y compound which is not reactive towards the halohydrin function of the compound of the formula:

(12)

and selected such that R2-O—Y may react with the terminal phosphate of this compound (12) in order to obtain the compound (15):

(15)

and substituents for which there is a compound R2-O-PPP, where PPP denotes the triphosphate group.

Said compounds according to the invention are advantageously wherein n=2 and R1 is $CH_3$.

The compounds according to the invention advantageously additionally comprise at least one group selected from among the group comprising nucleoside derivatives, oligonucleotides, nucleic acids (RNA, DNA), amino acids, peptides, proteins, monosaccharides, oligosaccharides, polysaccharides, fatty acids, simple lipids, complex lipids, folic acid, tetrahydrofolic acid, phosphoric acids, inositol, vitamins, co-enzymes, flavonoids, aldehydes, halohydrins and epoxides.

In particular, the invention provides the phosphoepoxide compounds of the formula (5) above in which R2 is selected from among the group comprising nucleoside derivatives, oligonucleotides, nucleic acids (RNA, DNA), amino acids, peptides, proteins, monosaccharides, oligosaccharides, polysaccharides, fatty acids, simple lipids, complex lipids, folic acid, tetrahydrofolic acid, phosphoric acids, inositol, vitamins, co-enzymes, flavonoids, aldehydes, halohydrins, phosphoepoxides of the formula (1) and epoxides.

The invention also provides compounds, the structure of which incorporates two or more groups of the formula (1), which may be identical or different, for example monomers, polymers, oligomers or dendrimers, or more generally molecules with two or more phosphorylated branches of the formula (1).

It should be noted that the compounds according to the invention are esters (monoesters or diesters) of phosphoric acid (this term encompassing those acids in which phosphorus is in oxidation state V, namely orthophosphoric acid, pyrophosphoric acid, metaphosphoric acid, triphosphoric acid, other polyphosphoric acids).

The invention provides a process for the production of the compounds according to the invention. This process is characterized in that:
  an intermediate compound comprising at least one phosphohalohydrin group of the formula is first prepared:

(6)

where X is a halogen selected from among iodine, bromine and chlorine,
  the intermediate compound is reacted with a hydroxide-producing medium in order to convert the halohydrin functions of the intermediate compound into epoxide functions.

Advantageously and according to the invention, in order to prepare said intermediate compound, the halogen $X_2$ is reacted in the presence of water with a starting compound comprising at least one phosphorylated alkene group of the formula:

(7)

Advantageously and according to the invention, a salt formed from said starting compound is reacted in an aqueous or aqueous/alcoholic medium, at neutral pH, at a temperature of below 30° C., by mixing with an aqueous solution of the halogen $X_2$. Advantageously and according to the invention, the reaction is performed at atmospheric temperature at a temperature of between 0° C. and 25° C.

The starting compounds may themselves be obtained from alcohol:

(16)

Advantageously and according to the invention, the starting compound is a salt of the formula:

(9)

The intermediate phosphohalohydrin compound of the following formula is then obtained:

(10)

An example of a complete reaction scheme for obtaining the intermediate compound (10) from the alcohol (16) is given below:

where TsCl is tosyl chloride,

4-DMAP is 4-dimethylaminopyridine,

$Bu_4N+$ is tetrabutylammonium, $(Bu_4N+)_3HP_2O_7$ is tris(tetra n-butylammonium) hydrogenpyrophosphate,

PP represents the pyrophosphate group.

The reactions which allow compound (9) to be obtained from the alcohol (16) may be performed as described by: DAVISSON V. J. et al. "Phosphorylation of Isoprenoid Alcohols" J. Org. Chem 1986, 51, 4768–4779, and DAVISSON V. J. et al. "Synthesis of Allylic and Homoallylic Isoprenoid Pyrophosphates" Methods in Enzymology, 1984, 110, 130–144.

Starting from the intermediate compound (10), the compound of the formula (2) according to the invention is obtained in accordance with the following scheme:

Advantageously and according to the invention, the starting compound is a salt of the formula:

The triphosphohalohydrin compound of the following formula is then obtained:

The triphosphoepoxide compound (4) according to the invention is then obtained.

An example of a complete reaction scheme for obtaining the compound (4) according to the invention from the alcohol (16) is given below:

where PPP is the triphosphate group, $(Bu_4N+)_4HP_3O_{10}$ is tetrakis(tetra-n-butylammonium) hydrogentriphosphate. The compound (8) is obtained from the alcohol (16) as stated above.

Starting from the intermediate compound (12), the triphosphoepoxide compound according to the invention of the formula (4) is obtained in accordance with the following scheme:

Several variants are possible for preparing a phosphoepoxide compound according to the invention of the formula (5).

In a first variant, a phosphohalohydrin intermediate compound of the following formula is first prepared:

$$X-CH_2-\underset{\underset{R_1}{|}}{\overset{\overset{OH}{|}}{C}}-(CH_2)_n-O-\underset{\underset{O^-Cat^+}{|}}{\overset{\overset{O}{\|}}{P}}-O-\underset{\underset{O^-Cat^+}{|}}{\overset{\overset{O}{\|}}{P}}-O-\underset{\underset{O^-Cat^+}{|}}{\overset{\overset{O}{\|}}{P}}-O-R2 \quad (15)$$

The compound (5) is thus obtained in accordance with the following reaction:

$$R_1-\underset{\underset{OH}{|}}{\overset{\overset{CH_2X}{|}}{C}}-(CH_2)_n-OPPP-OR_2 \quad \xrightarrow[\theta \leq 25°C]{OH^- \text{ basic medium}}$$

(15)

$$R_1-\overset{\overset{CH_2-O}{\diagdown \diagup}}{C}-(CH_2)_n-OPPP-O-R_2$$

(5)

To this end, the process may be performed as stated above (reaction of $X_2$ in the presence of water with a phosphorylated alkene function) by using a salt of the following formula as the starting compound:

$$CH_2=\underset{R_1}{\overset{|}{C}}-(CH_2)_n-O-\underset{\underset{O^-Cat^+}{|}}{\overset{\overset{O}{\|}}{P}}-O-\underset{\underset{O^-Cat^+}{|}}{\overset{\overset{O}{\|}}{P}}-O-\underset{\underset{O^-Cat^+}{|}}{\overset{\overset{O}{\|}}{P}}-O-R2 \quad (14)$$

where R2 is an organic or inorganic substituent of a nature such as not to prevent formation of the halohydrin function $$X-CH_2-\underset{\underset{R_1}{|}}{\overset{\overset{OH}{|}}{C}}-$$

starting from the alkene function $$CH_2=\underset{R_1}{\overset{|}{C}}$$

and halogen $X_2$ in the presence of water.

The starting compound (14) may itself be prepared in accordance with one of the following reaction schemes:

-Reaction scheme 1:

$$R_1-\overset{\overset{CH_2}{\|}}{C}-(CH_2)_n-OPPP \quad \xrightarrow[\text{acetonitrile}]{R_2-O-Ts}$$

(11)

$$R_1-\overset{\overset{CH_2}{\|}}{C}-(CH_2)_n-OPPP-O-R_2$$

(14)

where Ts is tosyl.

The compound (11) may be obtained as stated above starting from the alcohol (16) and the intermediate compound (8). The reaction which allows compound (14) to be obtained from the compound (11) may be performed under conditions similar to those described in the publications by DAVISSON V. J. et al. This scheme may be used when R2-O-Ts is commercially available.

-Reaction scheme 2:

$$R_1-\overset{\overset{CH_2}{\|}}{C}-(CH_2)_n-OTs \quad \xrightarrow[\text{acetonitrile}]{R_2-O-PPP, Bu_4N^+ \text{ salt}}$$

(8)

$$R_1-\overset{\overset{CH_2}{\|}}{C}-(CH_2)_n-OPPP-O-R_2$$

(14)

The intermediate compound (8) may be obtained as stated above starting from the alcohol (16). The reaction which allows compound (14) to be obtained from the compound (8) may be performed under conditions similar to those described in the publications by DAVISSON V. J. et al. This scheme may be used when R2-O-PPP is commercially available.

-Reaction scheme 3:

$$R_2-O-PPP \text{ triethylammonium salt} \quad \xrightarrow{\text{carbodiimide}}_{\text{DMF/MeOH}} \quad R_2-O-P\overset{P}{\underset{P}{\diagup}}$$

trimetaphosphate $$R_1-\overset{\overset{CH_2}{\|}}{C}-(CH_2)_n-OH \quad + \quad R_2-O-P\overset{P}{\underset{P}{\diagup}} \quad \xrightarrow[\text{DMF}]{\text{triethylamine}}$$

(16) trimetaphosphate $$R_1-\overset{\overset{CH_2}{\|}}{C}-(CH_2)_n-OPPP-O-R_2$$

(14)

where DMF is dimethylformamide,

MeOH is methanol.

This reaction scheme 3 may be performed under conditions similar to those described in D. G. KNORRE et al "General method for the synthesis of ATP gamma derivatives" Febs letters, 1976, 70, 105–108.

This reaction scheme 3 cannot be used when R2 comprises a carbodiimide-reactive function (carboxylate, triphosphate etc.). It is, however, advantageous when R2-O-PPP is commercially available.

In the specific case where R2- is itself an epoxide group of the formula:

(18)

the following reaction scheme may be used:

The compound (5') is a particular instance of the compound (5) according to the invention.

It should be noted that, in all these reactions, acetonitrile may be replaced by any other aprotic dipolar solvent (dimethylformamide DMF, dimethyl sulfoxide DMSO etc.).

It should be noted that when preparing compounds (2), (4) and (5') and in the event that n≠2, the intermediate compound (8) may also be replaced by the chloride or bromide compound of the formula:

(19)

where A is chlorine or bromine.

The alcohols (16) are commercially available or may readily be obtained by a well known Grignard reaction between an alkenyl organomagnesium compound and formaldehyde or ethylene oxide.

In a second variant, a compound of the formula (15) could be prepared by reacting the intermediate triphosphohalohydrin compound of the formula (12) starting from a salt soluble in an organic medium, such as a $Bu_4N+$ salt, in a subsequent stage with a compound R2-O—Y, where —O—Y is a leaving group and R2 is an organic or inorganic substituent selected such that R2-O—Y is capable of forming, by reaction with the compound (12), the intermediate compound of the formula (15).

In order to be capable of forming the intermediate compound of the formula (15) in this manner, the compound R2-O—Y must in particular not be reactive towards the halohydrin function:

Moreover, R2-O—Y must react with the terminal phosphate of compound (12) to form the compound (15).

The reaction of the compound of the formula (12) with R2-O—Y is a nucleophilic substitution. This reaction is in particular possible and advantageous for R2 selected from among the group comprising alkyls and alkenes. Y is selected such that R2-O—Y may give rise to the compound (15) by nucleophilic substitution. Y is selected, for example, from among tosyl, brosyl and triflyl.

This second variant then permits the phosphoepoxide compound according to the invention of the formula (5) to be prepared by reacting the intermediate compound (15) in a basic aqueous medium in order to convert the halohydrin functions of the intermediate compound (15) into epoxide functions as stated above.

In a third variant, the phosphoepoxide according to the invention may be prepared, without passing via the intermediate compound (15), starting from the alcohol (16) in accordance with the following reaction scheme:

This third variant is in particular advantageous when R2-O-PPP is commercially available or when it is not possible to prepare the phosphohalohydrin intermediate compound (15).

The first stage of this reaction which involves converting the alkene function into an epoxide function may be performed as stated by M. MUEHLBACHER et al. "Isopentenyl-diphosphate isomerase: inactivation of the enzyme with active-site-directed irreversible inhibitors and transition-state analogs", Biochemistry, vol. 27, no. 19, p 7315–7328 (1988).

This reaction scheme may also be used directly to obtain the monoester compounds (2) and (4) according to the invention. Nevertheless, with these monoester compounds, production starting from phosphohalohydrin intermediate compounds is generally faster, more quantitative and easier to perform.

In a fourth variant, the following reaction scheme is used:

This reaction may be performed under the conditions described by D. G. KNORRE et al "General method for the synthesis of ATP gamma derivatives" Febs letters, 1976, 70, 105–108.

A compound according to the invention may accordingly be difunctional or polyfunctional. The phosphoepoxide function(s) bring(s) about a specific desired antigenic property towards Tγ9δ2 lymphocytes, and R2 or the other functional groups of the compound may exhibit other, in particular therapeutic, properties.

In the case of a compound according to the invention having two or more phosphoepoxide groups of the formula (1), it is sufficient to start from a starting compound having the corresponding number of phosphorylated alkene groups of the formula (7) and the corresponding chemical structure, or to use the compound of the formula (12) and to react it with an intermediate compound R2-O—Y having the corresponding number of —O—Y functions (second variant), or to use a compound R2-O—PPP which already contains other epoxide functions (third and fourth variants).

The invention also in particular relates to the novel phosphoepoxide β ester compounds of the formula:

where R1 is selected from among —CH$_3$ and —CH$_2$—H$_3$, n is an integer between 2 and 20.

These compounds may be obtained in accordance with the following process:

The invention also provides uses of the compounds according to the invention as primate Tγ9δ2 lymphocyte activators, in particular to activate proliferation and/or cytotoxic activity and/or production of mediator substance(s) for primate Tγ9δ2 lymphocytes with TCR receptors comprising Vγ9 and Vδ2 variable regions.

The invention also provides uses of the compounds according to the invention for the treatment of cells sensitive to primate Tγ9δ2 lymphocytes in a natural or artificial medium which may contain Tγ9δ2 lymphocytes, in which medium said cells may be brought into contact with Tγ9δ2 lymphocytes and which is compatible with the compounds according to the invention (i.e. which is not likely to cause the breakdown thereof, at least under certain treatment conditions).

A "cell sensitive to Tγ9δ2 lymphocytes" is taken to mean any cell subject to the induced effector activity of the Tγ9δ2 lymphocytes: cell death (cell destruction by Tγ9δ2 lymphocytes); reception of cytokine released by Tγ9δ2 lymphocytes (TNF-α, INF-γ . . . ); possibly cellular proliferation induced by Tγ9δ2 lymphocytes.

The invention accordingly provides a Tγ9δ2 lymphocyte activation process, in particular a process for activating the proliferation of Tγ9δ2 lymphocytes and/or the cytotoxic activity of Tγ9δ2 lymphocytes and/or the production of mediator substance(s) by Tγ9δ2 lymphocytes, in which process these Tγ9δ2 lymphocytes are brought into contact with at least one compound according to the invention in a medium which contains Tγ9δ2 lymphocytes and is compatible with T lymphocyte growth. Advantageously and according to the invention, interleukin, in particular interleukin-2 (IL-2), is introduced into the medium in a proportion suitable to bring about lymphocyte growth in this medium. Indeed, the presence of the lymphocyte growth factor IL-2 is essential to achieve proliferation of the T lymphocytes, among which only the Tγ9δ2 lymphocytes have been activated by a compound according to the invention. This growth factor must thus be present in the medium for those uses in which proliferation of Tγ9δ2 lymphocytes is desired. This lymphocyte growth factor may pre-exist in the natural state or be induced or introduced into the medium, simultaneously or not with the incorporation of the compound according to the invention, in the same therapeutic composition or not. Nevertheless, in certain uses in which activation without proliferation of the Tγ9δ2 lymphocytes is desired (for example induced cytotoxicity), the presence of this growth factor is not helpful.

More specifically, the invention provides uses of the compounds according to the invention for therapeutic purposes for the curative or preventive treatment of pathological conditions producing cells sensitive to primate Tγ9δ2 lymphocytes in a medium which may contain these Tγ9δ2 lymphocytes and in which these cells may be brought into contact with the Tγ9δ2 lymphocytes.

Advantageously and according to the invention, at least one compound according to the invention is used at a concentration in the medium which brings about activation of polyclonal proliferation of Tγ9δ2 lymphocytes. This medium may be selected from among human blood, non-human primate blood, human blood extracts, non-human primate blood extracts.

Said medium may be extracorporeal, said activation process according to the invention then being an extracorporeal cellular treatment, in particular applicable in a laboratory, for studying Tγ9δ2 lymphocytes or the properties thereof, or for diagnostic purposes. The invention also provides a composition for extracorporeal (ex vivo) diagnostics, wherein it comprises at least one compound according to the invention.

Said medium may also be intracorporeal, activation of the Tγ9δ2 lymphocytes then being of therapeutic use.

More particularly, said medium is the peripheral bloodstream of a primate. The invention accordingly in particular provides a process for the activation of Tγ9δ2 lymphocytes in the peripheral bloodstream of a primate, in particular humans, into which is administered at least one compound according to the invention in a quantity suitable for activating Tγ9δ2 lymphocytes. At least one compound according to the invention is thus administered by a general route, in particular parenterally into the peripheral bloodstream.

Said medium may also comprise a cellular site to be treated and at least one compound according to the invention is administered directly in contact with the cellular site to be treated (topical administration).

The invention accordingly in particular provides therapeutic uses of the compounds according to the invention for treating pathological conditions in primates, said conditions belonging to the group comprising cancers, infectious diseases, in particular mycobacterial infections (leprosy, tuberculosis etc.); parasitic conditions (malaria etc.); pathological immunodeficiency syndromes (AIDS etc.). According to the invention, a therapeutic composition is administered which is suitable for releasing into the peripheral bloodstream and/or at a cellular site to be treated a quantity of at least one compound according to the invention capable of activating Tγ9δ2 lymphocytes. Indeed, it has been demonstrated in general terms in the above-stated prior art that a composition having the property of activating Tγ9δ2 lymphocytes may advantageously be used for treating these pathological conditions.

As is conventional, throughout the text the terms "therapy" or "therapeutic" encompass not only curative treatment or care, but also preventive treatment (prophylaxis), such as vaccination, together with intracorporeal diagnostics (administration for diagnostic purposes). Indeed, by permitting activation of Tγ9δ2 lymphocytes, the invention allows immunostimulatory treatments which may be advantageous not only prophylactically by preventing the development of pathogenic cells sensitive to Tγ9δ2 lymphocytes, but also curatively by inducing destruction of pathogenic cells sensitive to Tγ9δ2 lymphocytes.

The invention accordingly provides a therapeutic composition comprising at least one compound according to the invention. More specifically, the invention relates to a therapeutic composition comprising a quantity capable of being administered to a primate, in particular in contact with the peripheral bloodstream or topically, of at least one compound according to the invention, in particular for the preventive or curative treatment of the above-stated pathological conditions. A composition according to the invention may be an immunostimulant composition or a vaccine, the compounds according to the invention being antigens which activate Tγ9δ2 lymphocytes.

Advantageously and according to the invention, the therapeutic composition is characterized in that it moreover comprises a proportion of interleukin, in particular interleukin-2, suitable for bringing about lymphocyte growth in the medium into which it is to be administered.

A therapeutic composition according to the invention may be prepared in a dosage form capable of being administered by a general route, in particular parenterally directly into the peripheral bloodstream of a primate, with at least one compound according to the invention in a quantity suitable to activate Tγ9δ2 lymphocytes and one or more appropriate excipient(s). Given the very low active concentration of the compounds according to the invention (of the order of 1 to 100 nM), such administration may be made without risk of toxicity.

A therapeutic composition according to the invention may also be prepared in a dosage form appropriate for topical administration, directly in contact with the cells sensitive to Tγ9δ2 lymphocytes.

The dosage form of a therapeutic composition according to the invention is produced in accordance with the selected route of administration using conventional pharmaceutical formulation methods. The quantity and concentration of compound(s) according to the invention and the dosage are determined by reference to known chemotherapeutic methods for the diseases to be treated, taking account of the bioactivity of the compounds according to the invention towards Tγ9δ2 lymphocytes, the individual to be treated, the disease in question and the desired biological effects.

Advantageously and according to the invention, in the case of a bioactive compound at a concentration of between 10 nM and 100 nM, the quantity of compound(s) according to the invention administered by a general route is between 1 μg and 1000 μg, in particular between 10 μg and 100 μg, per kilogram of patient body weight.

It has moreover been demonstrated in vitro that the compounds according to the invention exhibit no general toxicity even at concentrations of up to 100 μM, i.e. of the order of $10^4$ times the bioactive concentration. Furthermore, it is known that the biochemical class of molecules to which the compounds according to the invention belong (phosphoesters) comprises a family of metabolic compounds found in any living cell. The compounds according to the invention thus exhibit no toxic effects other than those induced by the bioactivity thereof upon Tγ9δ2 lymphocytes.

Moreover, certain compounds according to the invention have a sufficiently low molecular weight (in particular below 500) to be compatible with the elimination thereof via the kidneys and urine.

One example formulation of an injectable therapeutic composition according to the invention for a primate weighing 1 kg is as follows: 50 μg of 3,4-epoxy-3-methyl-1-butyl diphosphate (Epox-PP) diluted in 0.5 ml of sterile phosphate buffer at pH 7 and adjusted to 37° C.

In this manner, 50 μg of Epox-PP (compound of the formula (2)) are administered per 1 kg of animal body weight, corresponding to a concentration in the circulating blood such as to be greater than the bioactive concentration of Epox-PP (a concentration of 100 nM of Epox-PP corresponding to approx. 50 ng/ml).

It should be noted that the excipients or other conventionally used pharmaceutically acceptable additives are chemically compatible with the compounds according to the invention.

A therapeutic composition according to the invention may also advantageously comprise one or more other active ingredient(s), in particular to bring about a synergistic effect. In particular, a compound according to the invention may act as a vaccine adjuvant. The therapeutic vaccine composition according to the invention then comprises a known vaccine composition to which is added a quantity of compound(s) according to the invention capable of activating the Tγ9δ2 lymphocytes which will not only be able to exert their anti-infective activity directly, but will also be able to activate the T lymphocytes which effect the conventional vaccine response.

A therapeutic composition according to the invention may also itself incorporate primate Tγ9δ2 lymphocytes in a culture in a medium compatible with T lymphocyte growth.

It may then be used for treating primates, or more generally vertebrates with which administration of primate Tγ9δ2 lymphocytes may be performed under conditions of immune compatibility towards said primate Tγ9δ2 lymphocytes. Such a composition according to the invention may be administered by a general route, or even by a topical route, in contact with target pathogenic cells, sensitive to said primate Tγ9δ2 lymphocytes.

The invention also provides the use of at least one compound according to the invention for the production of a therapeutic composition according to the invention. More particularly, the invention relates to the use of at least one compound according to the invention for the production of a therapeutic composition intended for the preventive or curative treatment of a pathological condition of humans or vertebrates which produces cells sensitive to primate Tγ9δ2 lymphocytes, in particular a pathological condition selected from the group comprising cancers, infectious diseases, parasitic conditions and pathological immunodeficiency syndromes. To this end, the invention also provides the use of at least one compound according to the invention for the production of a therapeutic composition intended to be administered, in particular in contact with the peripheral bloodstream or by a topical route, to a primate, in particular to humans, for the preventive or curative treatment of a pathological condition as mentioned above.

The invention also provides a process for the production of a composition, in particular a therapeutic composition, according to the invention having the characteristic of activating Tγ9δ2 lymphocytes, in which process at least one compound according to the invention is used.

The invention also relates to a process for the production of a therapeutic composition intended for the preventive or curative treatment of a pathological condition of humans or vertebrates which produces cells sensitive to primate Tγ9δ2 lymphocytes, in which process at least one compound according to the invention is used. The invention in particular relates to a process for the production of a therapeutic composition intended to be administered, in particular in contact with the peripheral bloodstream or by a topical route, to a primate for the preventive or curative treatment of a pathological condition which produces cells sensitive to Tγ9δ2 lymphocytes, in particular a pathological condition belonging to the group stated above, in which process at least one compound according to the invention is used.

Advantageously and according to the invention, in a production process according to the invention, at least one compound according to the invention is brought into contact with a medium which contains primate Tγ9δ2 lymphocytes, and is compatible with T lymphocyte growth, in a quantity suitable to activate these Tγ9δ2 lymphocytes in this medium. Advantageously and according to the invention, said medium comprises a substance selected from among primate blood and primate blood extracts. A therapeutic composition containing activated Tγ9δ2 lymphocytes is then obtained so allowing a cellular therapeutic approach to be performed.

It should be noted that the compounds according to the invention are epoxide compounds and do not correspond to natural phosphoantigens, in particular to the molecules known as Tubag1, Tubag2, Tubag3 and Tubag4 obtained as described in WO 95/20673. It is in any event possible to demonstrate for example that these natural phosphoantigens are broken down by bromine water or by treatment with sodium borohydride in a basic aqueous medium, whereas the compounds according to the invention are insensitive to these reagents. The compounds according to the invention are thus not natural antigens, but are synthetic antigens which activate Tγ9δ2 lymphocytes at concentrations of the same order and with an efficiency similar to or even greater than that of natural antigens.

It should also be noted that, contrary to the prior art as illustrated by U.S. Pat. No. 5,639,653, which considered that the presence of an alkyl or alkene group was essential to activate human Tγ9δ2 lymphocytes, the inventors have observed that by destroying the alkene bond and replacing it with an epoxide group, the Tγ9δ2 lymphocytes are activated extremely strongly and at very low concentration. In particular, it may be observed that the effect may even exceed that of phosphoantigens of natural origin.

BRIEF DESCRIPTION OF THE DRAWINGS

Further features, objects and advantages of the invention will be evident from the following Examples, which are provided in non-limitative manner merely for purposes of explanation, and from the figures.

EXAMPLES

Example 1

Production of 3,4-epoxy-3-methyl-1-butyl diphosphate (Epox-PP)

Preparation of 3-methyl-3-butene-1-yl tosylate (isopentenyl tosylate)

2.32 mmol (442 mg) of tosyl chloride and 2.55 mmol (312 mg) of 4-(N,N-dimethylamino)pyridine are introduced while stirring with a magnetic stirrer into 5 ml of anhydrous dichloromethane in a glass reaction vessel which is equipped for handling under an inert atmosphere and has been carefully dried. 2.32 mmol (200 mg) of isopentenol dissolved in approx. 1 ml of dichloromethane are slowly added to this mixture through a septum using a syringe. The reaction is monitored by thin-layer chromatography on silica (silica gel 60 F-254; eluent: pentane/ethyl acetate 85/15 vol./vol.; $R_f$ (product)=0.4 and $R_f$ (TsCl)=0.5). After approx. 3 hours' stirring under a nitrogen atmosphere, the reaction mixture is diluted in a large volume of hexane (approx. 100 ml), resulting in the immediate formation of a white precipitate. The mixture is then filtered and the filtrate concentrated by evaporation under reduced pressure. The solution is then diluted with diethyl ether and refiltered. Once the solvent has evaporated, a yellowish oil is obtained. The product is purified by preparative chromatography through a silica column (silica gel 60; eluent: pentane/ethyl acetate 85/15). In this manner, 1.98 mmol (475 mg) of 3-methyl-3-butene-1-yl tosylate (85% isolated yield) are obtained. The compound (colorless oil) is stored at +4° C. in an anhydrous medium.

Preparation of tris(tetra-n-butylammonium) hydrogenpyrophosphate 4.5 mmol (1 g) of dihydrogenpyrophosphate disodium salt ($Na_2H_2P_2O_7$) are dissolved in 10 ml of cold deionized water which has previously been adjusted to pH 9 with a 10 mM ammonia solution. The solution is passed through a column containing 19 milliequivalents (4 g) of DOWEX® 50-WX8–200 cationic resin (H$^+$ form). The acid solution is eluted with 15–20 ml of cold deionized water at pH 9. The collected solution is immediately titrated at pH 7.3 using a 40% aqueous solution of tetra-n-butylammonium hydroxide (Bu$_4$NOH). After freeze-drying, 4 g of tetra-n-butylammonium salt are obtained as a hygroscopic white solid. The salt is dissolved in 10 ml of anhydrous acetonitrile. The solution is subsequently filtered, then dried by evaporation of the solvent under reduced pressure in successive stages. In this manner, a solution of tris(tetra-n-butylammonium) hydrogenpyrophosphate is obtained with a purity of 98% (result deduced from analysis by ionic chromatography (HPAEC)). The volume is adjusted to achieve a salt concentration of between 0.5 and 1 M. The solution is stored at –20° C. in an anhydrous medium.

Preparation of 3-methyl-3-butene-1-yl diphosphate (isopentenyl pyrophosphate)

2.5 ml of a solution of tris(tetra-n-butylammonium) hydrogenpyrophosphate at a concentration of 0.7 M (1.75 mmol) in anhydrous acetonitrile are introduced into a glass reactor which has been dried carefully. The reactor is cooled with an ice bath, then 0.70 mmol (168 mg) of 3-methyl-3-butene-1-yl tosylate dissolved in a minimum quantity of acetonitrile (0.5–1 M) are added using a syringe, while stirring with a magnetic stirrer. Once the tosylate has been introduced, the ice bath is removed, then the reaction is allowed to continue at room temperature with stirring. The progress of the reaction is then monitored by ionic chromatography (HPAEC). After approx. 3 hours, the solvent is evaporated under reduced pressure and the reaction medium redissolved in 3 ml of a 98/2 (vol./vol.) water/2-propanol mixture. The solution is passed through a column containing 19 milliequivalents (4 g) of DOWEX® 50-WX8-200 cationic resin (NH$_4^+$ form), then eluted with 10 ml of the water (pH 9)/2-propanol 98/2 (vol./vol.) mixture. After freeze-drying, a white solid containing the crude product is collected.

Purification:

The pyrophosphate and the traces of ammonium monophosphate are separated from the medium by coprecipitation in the presence of ammonium hydrogencarbonate. The crude product obtained in the preceding stage is dissolved in 4 ml of 0.1 M ammonium hydrogencarbonate, which is transferred into a 25 ml centrifuge tube. The solution is then treated with 10 ml of a 1/1 (vol./vol.) acetonitrile/2-propanol mixture by shaking the mixture vigorously (vortex) for a few minutes until a white precipitate has formed. The tube is then centrifuged at 2000 rpm at 10° C. for 5 minutes. The supernatant, into which the organic salts have been extracted, is stored at +4° C. The procedure is repeated by redissolving the precipitate in 3 ml of 0.1 M ammonium hydrogencarbonate, to which 7 ml of the acetonitrile/2-propanol mixture are added. The two supernatants are combined and the solvent evaporated under a vacuum. An oily liquid is obtained which is stored at +4° C.

The ammonium tosylate is separated from the reaction medium by extraction with the 1/1 (vol./vol.) chloroform/methanol solvent. The oily liquid from the preceding stage is dissolved in 4 ml of water at pH 9 and treated with 1 ml of this solvent by a conventional extraction procedure which is repeated 3 times. Any traces of solvent are then removed from the aqueous phase by evaporation under reduced pressure at 30° C. On the basis of analysis by ionic chromatography (HPAEC), an 83% yield of 3-methyl-3-butene-1-yl diphosphate (0.58 mmol, 172 mg) is obtained. The solution is stored at –20° C.

The product is then purified in accordance with requirements by anion exchange chromatography through 360 mg to 10 g Sep-Pak Accell Plus QMA (Waters®) cartridges eluted in succession respectively by 20 mM, 40 mM, 100 mM then 200 mM aqueous ammonium hydrogencarbonate solutions, with the eluted fractions being monitored by chromatography (HPAEC). The fractions corresponding to the purified product are combined and then freeze-dried.

Preparation of 3-(bromomethyl)-3-butanol-1-yl diphosphate 0.34 mmol (100 mg) of isopentenyl pyrophosphate (ammonium salt) dissolved in 2 ml of neutral pH deionized water are treated under a fume hood at room temperature with 1.9 ml (0.34 mmol) of bromine in a saturated aqueous solution (0.18 M). The bromine solution is added gradually with the mixture being stirred periodically until the bromine water has become colorless. In the event that bromine is added in a slight excess (persistent yellow color), the solution is transferred into a glass flask and then exposed to reduced pressure (rotary evaporator) for a few minutes at a temperature of 30° C. until the color disappears. The aqueous solution is filtered and then neutralized by being passed through a DOWEX® 50-WX8-200 cationic resin column (NH$_4^+$ form) eluted by two column volumes of deionized water. A solution of 3-(bromomethyl)-3-butanol-1-yl diphosphate (0.33 mmol, 130 mg) is obtained quantitatively and stored at –20° C.

Production of 3,4-epoxy-3-methyl-1-butyl diphosphate 1 ml of the aqueous solution containing 3.35 mg (8.5 μmol) of 3-(bromomethyl)-3-butanol-1-yl diphosphate (ammonium salt) obtained in the preceding stage are treated at room temperature with 1 ml of a molar ammonia solution. The solution is stirred for a few minutes and then freeze-dried to remove the ammonia. The dry residue obtained after freeze-drying (2.7 mg, 8.5 μmol) is redissolved in 2 ml of deionized water. The bromide ions are removed from the solution using a DIONEX® apparatus comprising an OnGuard®-Ag cartridge attached to an OnGuard®-H cartridge (capacity 1.8 milliequivalents). The halide ions (bromides) are selectively retained as the solution passes through this apparatus, which is eluted with 1 ml of deionized water. For the purpose of performing biological testing, the aqueous solutions of the product are sterilized by filtration through a 0.2 μm filter and stored at –20° C. In the case of testing performed in vivo, the solutions are passed beforehand through a DOWEX® 50-WX8-200 cationic resin column (Na$^+$ form) eluted by two column volumes of deionized water.

Example 2

Production of 3,4-epoxy-3-methyl-1-butyl triphosphate (Epox-PPP)

Preparation of tetrakis(tetra-n-butylammonium) hydrogentriphosphate 2.1 mmol (1 g) of tripolyphosphate hexahydrate pentasodium salt (Na$_5$P$_3$O$_{10}$.6H$_2$O) are dissolved in 10 ml of cold deionized water which has previously been adjusted to pH 9 with a 10 mM ammonia solution. The solution is passed through a column containing 21 milliequivalents (4.4 g) of DOWEX® 50-WX8 cationic resin (H⁺ form). The acid solution is eluted with 20–25 ml of cold deionized water at pH 9. The collected solution is immediately titrated at pH 7.0 using a 40% aqueous solution of tetra-n-butylammonium hydroxide ($Bu_4NOH$). After freeze-drying, 2.5 g of tetra-n-butylammonium salt are obtained as a hygroscopic white solid. The salt is dissolved in 10 ml of anhydrous acetonitrile. The solution is subsequently filtered, then dried by evaporation of the solvent under reduced pressure in successive stages. In this manner, a solution of tetrakis(tetra-n-butylammonium) hydrogentriphosphate with a purity of 95% is obtained (result deduced from analysis by ionic chromatography (HPAEC)). The volume is adjusted to achieve a salt concentration of between 0.5 and 1 M. The solution is stored at −20° C. in an anhydrous medium.

Preparation of 3-methyl-3-butene-1-yl triphosphate (isopentenyl triphosphate)

Using the procedure described for the preparation of 3-methyl-3-butene-1-yl diphosphate (Example 1), 2 mmol of a molar solution of tetrakis(tetra-n-butylammonium) hydrogentriphosphate are reacted under a nitrogen atmosphere with 1 mmol (240 mg) of 3-methyl-3-butene-1-yl tosylate prepared according to Example 1 in 4 ml of anhydrous acetonitrile for 24 hours. By using a precipitation/extraction purification procedure similar to that applied to 3-methyl-3-butene-1-yl diphosphate, on the basis of analysis by ionic chromatography (HPAEC), a yield of 74% of 3-methyl-3-butene-1-yl triphosphate (0.74 mmol, 292 mg) is obtained. Phosphoepoxides according to the invention are prepared for the purpose of biological testing by using a fraction of the product obtained at this stage which is purified by HPAEC through an IonPac® AS11 column, with two or more chromatographic passes being combined. In this manner, approx. 2 ml of an aqueous millimolar solution of neutral pH of 3-methyl-3-butene-1-yl triphosphate are prepared in the form of an ammonium salt.

Preparation of 3-(bromomethyl)-3-butanol-1-yl triphosphate 500 nmol (500 µl of a millimolar solution) of isopentenyl triphosphate are treated at room temperature by addition of 500 nmol of bromine in a saturated aqueous solution (2.8 µl of 180 mM bromine water). Once the mixture has been stirred and the bromine has become colorless (virtally instantaneously), the product 3-(bromomethyl)-3-butanol-1-yl triphosphate is produced quantitatively (0.5 ml of a millimolar solution).

Preparation of 3,4-epoxy-3-methyl-1-butyl triphosphate

The solution obtained in the preceding stage containing 500 mmol of 3-(bromomethyl)-3-butanol-1-yl triphosphate is injected in several fractions into a Dionex® HPAEC system in accordance with "High pH anion exchange chromatographic analysis of phosphorylated compounds: application to isolation and characterization of non peptide mycobacterial antigens", Y. Poquet et al, Anal. Biochem, 243 no. 1, 1996, p. 119–126. The epoxide is formed quantitatively on each chromatographic pass and is collected in the presence of ammonium hydroxide or hydrogencarbonate. The collected fractions are freeze-dried. In this manner, approx. 1 ml of an aqueous 500 µM solution of 3,4-epoxy-3-methyl-1butyl triphosphate is obtained, which is treated as in Example 1 for the performance of biological testing and/or for the performance of in vivo testing and stored at −20° C.

Example 3

Production of α,γ di-(3,4-epoxy-3-methyl-1-butyl) triphosphate (di EpoxTP):

Preparation of α,γ di-(3-methyl-3-butene-1-yl) triphosphate

Using the procedure described for the preparation of 3-methyl-3-butene-1-yl diphosphate (Example 1), 0.5 mmol of a molar solution of tetrakis(tetra-n-butylammonium) hydrogentriphosphate (prepared according to Example 2) are reacted under a nitrogen atmosphere with 1 mmol (240 mg) of 3-methyl-3-butene-1-yl tosylate (prepared according to Example 1) in 4 ml of anhydrous acetonitrile for 24 hours. By using a precipitation/extraction purification procedure similar to that applied to 3-methyl-3-butene-1-yl diphosphate, on the basis of analysis by ionic chromatography (HPAEC), a yield of 81% of α,γ di-[3-methyl-3-butene-1-yl] triphosphate (0.4 mmol, 178 mg) is obtained. Phosphohalohydrin compounds according to the invention are prepared for the purpose of biological testing by using a fraction of the product obtained at this stage which is purified by HPAEC through an IonPac® AS11 column, with two or more chromatographic passes being combined. Before each chromatographic pass and in order to improve isolation of the product, the fraction to be purified is treated enzymatically with alkaline phosphatase in order to break down the isopentenyl triphosphate which is a secondary product of the reaction. In this manner, approx. 1 ml of an aqueous millimolar solution of neutral pH of α,γ di-[3-methyl-3-butene-1-yl] triphosphate are prepared in the form of an ammonium salt.

Preparation of α,γ di-[3-(bromomethyl)-3-butanol-1-yl] triphosphate 250 nmol (250 µl of a millimolar solution) of α,γ di-(3-methyl-3-butene-1-yl)triphosphate are treated at room temperature by addition of 250 nmol of bromine in a saturated aqueous solution (1.4 µl of 180 mM bromine water). Once the mixture has been stirred and the bromine has become colorless (virtually instantaneously), the product α,γ di-[3-(bromomethyl)-3-butanol-1-yl] triphosphate is produced quantitatively (250 µl of a millimolar solution).

Production of α,γ di-(3,4-epoxy-3-methyl-1-butyl) triphosphate

The solution obtained in the preceding stage containing 250 nmol of α,γ di-[3-(bromomethyl)-3-butanol-1-yl] triphosphate is injected in several fractions into a Dionex® DX500 HPAEC system as described in Example 2. In this manner, approx. 0.5 ml of an aqueous 500 µM solution of α,γ di-[3,4-epoxy-3-methyl-1-butyl] triphosphate is obtained, which is treated as in Example 1 for the performance of biological testing and/or for the performance of in vivo testing and stored at −20° C.

Example 4

Production of uridine 5'-triphosphate γ-(3,4-epoxy-3-methyl-1-butyl) (Epox-UTP)

Preparation of uridine 5'-triphosphate γ-(3-methyl-3-butene-1-yl)

This product is prepared in accordance with the procedure described by KNORRE D. C. et al. "General Method for the synthesis of ATP Gamma-derivatives" Febs Letters, 1976, 70–1, 105–108, starting from 40 μmol of uridine 5'-triphosphate (UTP) (triethylammonium salt) in the presence of an excess of isopentenol. Phosphoepoxide compounds according to the invention are prepared for the purpose of biological testing by purifying a fraction of the product obtained by HPAEC through an IonPac® AS11 column, with two or more chromatographic passes being combined. Before each chromatographic stage and in order to improve isolation of the product, the fraction to be purified is treated enzymatically with alkaline phosphatase in order to break down the secondary products (UDP and UMP) and unreacted UTP. In this manner, approx. 500 μl of an aqueous 300 μM solution of neutral pH of uridine 5'-triphosphate γ-(3-methyl-3-butene-1-yl) are prepared in the form of an ammonium salt.

Preparation of uridine 5'-triphosphate γ-[3-(iodomethyl)-3-butanol-1-yl]

75 nmol (250 μl of a 300 μM solution) of uridine 5'-triphosphate γ-3-methyl-3-butene-1-yl in ammonium salt form are treated in an aqueous medium of neutral pH by addition of 108 μl of 0.7 mM iodized water prepared according to Example 2. The solution is left for 20 minutes at room temperature while periodically being stirred vigorously. Once the iodized water has become colorless, the product uridine 5'-triphosphate γ-[3-(iodomethyl)-3-butanol-1-yl] is produced quantitatively (approx. 360 μl of a 200 μM solution).

Production of uridine 5'-triphosphate γ-(3,4-epoxy-3-methyl-1-butyl)

The solution obtained in the preceding stage containing 75 mmol of uridine 5'-triphosphate γ-[3-(iodomethyl)-3-butanol-3-yl] is injected in several fractions into a Dionex® DX500 HPAEC system as described in Example 2. In this manner, approx. 0.5 ml of an aqueous 150 μM solution of uridine 5'-triphosphate γ-(3,4-epoxy-3-methyl-1-butyl) is obtained, which is treated as in Example 1 for the performance of biological testing and/or for the performance of in vivo testing and stored at –20° C.

Example 5

Measurement of Antigenic Activity by Stimulation of the Proliferation of Tγ9δ2 Lymphocytes in a Culture 20 microliters of the aqueous solution of the compound according to the invention to be tested which has been adjusted to the final concentration specified in the test are added to an in vitro culture of $10^6$ total T lymphocytes in 1 ml, separated from the blood of a healthy adult human donor and initially containing 1–5% of Tγ9δ2 lymphocytes, in an adequate culture medium (RPMI 1640+10% of inactivated human serum and 50 U/ml of human interleukin-2 (hIL-2)). After culturing for 4 days, 50 U of hIL-2 are added per milliliter of culture medium. After 8 days, the cells are counted, collected, washed with phosphate buffer, and the Tγ9δ2 type cells are detected in the culture by labeling with conventional commercial reagents (fluorescein-labeled monoclonal antibodies) and the proportion thereof determined by flux cytometry analysis. The parameter measured is either the change in the proportion of or the increase in the number of Tγ9δ2 cells in cultures in the presence of the compound according to the invention in comparison with cultures not containing a compound according to the invention. The results of this testing are represented by plotting curves of these values (y-axis in FIG. 1) as a function of concentration on a logarithmic scale of the compound according to the invention placed in the culture x-axis in FIG. 1).

Figure 1:
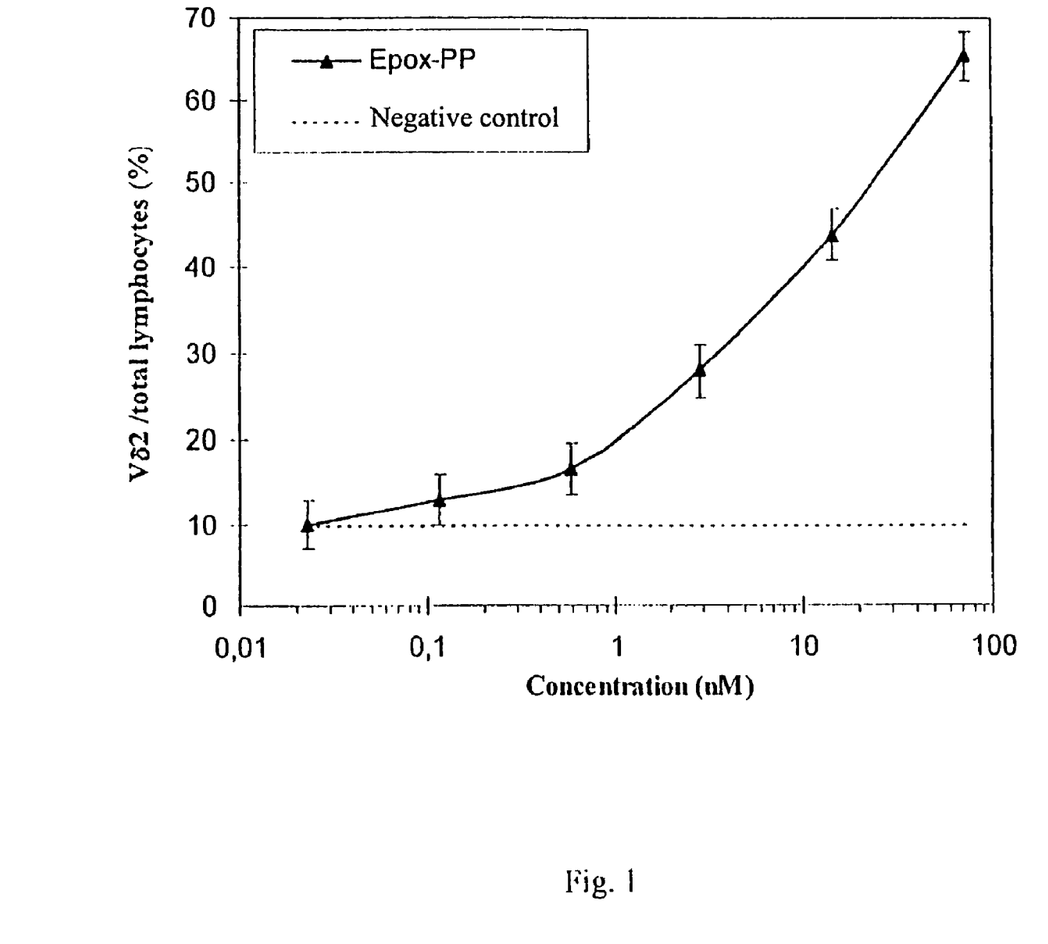
FIG. 1 is a graph showing the results obtained in Example 5.

FIG. 1 shows the results obtained with the compounds according to the invention obtained in Example 1 (Epox-PP), with the dotted line being a negative control (value obtained in the absence of the compound according to the invention).

Table 1 below shows the ED50 values, the effective dose at 50% of the maximum polyclonal lymphocyte amplification effect obtained as stated above with IPP (by way of comparison) and with various compounds according to the invention.

| MOLECULE | | | ED 50% |
|---|---|---|---|
| Name | Abbreviation | Structure | nM |
| isopentenyl pyrophosphate | IPP |  | 3000 |
| 3,4-epoxy-3-methyl-1-butyl diphosphate | Epox-PP |  | 20 |
| 3,4-epoxy-3-methyl-1-butyl triphosphate | Epox-PPP |  | 100 |

-continued

| MOLECULE | | | ED 50% |
|---|---|---|---|
| Name | Abbreviation | Structure | nM |
| α, γ di 3,4-epoxy-3-methyl-1-butyl triphosphate | di-EpoxTP | H₃C—C(CH₂—O)(CH₂)₂—OPPPO—(CH₂)₂—C(CH₂—O)—CH₃ | 2000 |

Example 6

Measurement of Antigenic Activity by Stimulation of Induced Cytotoxicity

Figure 2:
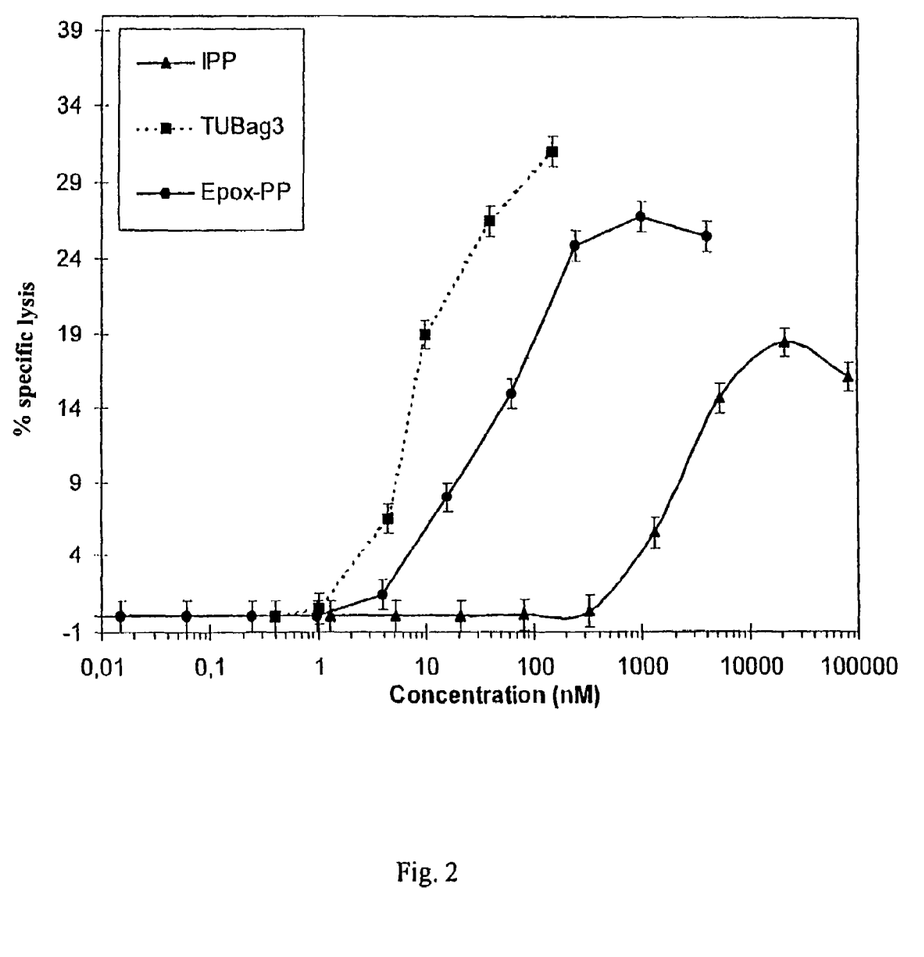
FIG. 2 is a graph showing the results obtained in Example 6.

The specific cytotoxic activity of a Tγ9δ2 lymphocyte clone measured in accordance with the induced cytotoxicity test is compared, said activity being stimulated with decreasing concentrations of the phosphoantigen Tubag3 obtained as described by WO 95/20673 (curve represented by black squares in FIG. 2), of the compound Epox-PP according to the invention obtained in Example 1 (curve represented by black circles in FIG. 2), and of isopentenyl pyrophosphate (IPP, curve represented by black triangles in FIG. 2).

It may be noted that the compound according to the invention from Example 1 is active at a concentration of the order of 20 nM, whereas the prior art compound IPP is active at a concentration of the order of 3 μM, or 150 times higher.

Example 7

Demonstration of the Difference in Structure Between an Epoxide Compound According to the Invention and the Natural Mycobacterial Tubag Phosphoantigens The bioactivity of the compound according to the invention Epox-PP (obtained as stated in Example 1) is compared with that of a stock preparation of Tubag natural phosphoantigens obtained as described in WO 95/20673.

Bioactivity is measured by an induced cytotoxicity test as described in Example 6 using the compound to be tested diluted 1:30 from 5 to 10 μM solutions of the compounds.

Before bioactivity is measured, the compounds are subjected to a transient chemical treatment by being brought into contact with one of the following reagents: NaIO₄ (5 mM); NaBH₃CN (10 mM, pH 7); KMnO₄ (1 mM); bromine water Br₂, H₂O (7 mM), followed by neutralization of the reagent.

The following table shows the results obtained from several independent tests performed in each case. + indicates detection of activity upon Tγ9δ2 lymphocytes; − indicates that no activity could be detected.

| | Bioactivity after chemical treatment: | | | | |
|---|---|---|---|---|---|
| REAGENT | none | NAIO₄ (5 mM) | NaBH₃CN (10 mM pH 7) | KMnO₄ (1 mM) | Br₂,H₂O (7 mM) |
| Tubag | + | + | + | − | − |
| Epox-PP | + | + | + | + | + |

It may be noted that treating the natural mycobacterial Tubag phosphoantigens with dilute KMnO₄ or bromine water completely curtails the bioactivity thereof. In contrast, the phosphoepoxide compounds according to the invention, which have a stimulant action at concentrations of the order of 20 nM, resist the same chemical treatment, so demonstrating the difference in chemical structure between the synthetic compounds according to the invention and the natural Tubag compounds.

Example 8

Toxicity of Epox-PP (Sodium Salt)

Five 30 g mice received an intravenous injection (caudal vein) of 300 μl of PBS buffer containing 1 mg of Epox-PP (sodium salt). No sign of shock or pyrogenicity is observed: 5 mice are still alive after 30 days; no significant variation in the weight of the mice is recorded during the study. Toxicity is thus less than 20% for a dose of 33.4 mg of Epox-PP (sodium salt) per kilogram of animal body weight.

The invention claimed is:

1. A method for activating a Tγ9δ2 lymphocyte in vitro, comprising:
    contacting in vitro a Tγ9δ2 lymphocyte with an effective amount of a compound comprising at least one phosphoepoxide group, said compound having a formula selected from the group consisting of
    (a) a compound having the following formula:

(2)

wherein R1 is selected from among —CH₃ and —CH₂CH₃, Cat⁺ is a cation, and
n is an integer between 2 and 20;
(b) a compound having the following formula:

(4)

wherein R1 is selected from among —CH₃ and —CH₂CH₃, Cat⁺ is a cation, and
n is an integer between 2 and 20; and
(c) a compound having the following formula:

(5)

wherein R1 is selected from among —CH$_3$ and CH$_2$CH$_3$,
Cat$^+$ is a cation, and
n is an integer between 2 and 20, and
R2 is a biomolecule.

2. The method according to claim 1, wherein said compound is brought into contact with a Tγ9δ2 lymphocyte in the presence of a T lymphocyte growth factor.

3. The method according to claim 2, wherein said T lymphocyte growth factor is IL-2.

4. The method according to claim 1, wherein said compound is introduced into a medium containing said Tγ9δ2 lymphocytes and cells.

5. The method according to claim 1, wherein said compound and said Tγ9δ2 lymphocyte are introduced into a medium that allows for T lymphocyte growth.

6. A compound of the formula:

(4)

wherein R1 is selected from among —CH$_3$ and CH$_2$CH$_3$,
Cat$^+$ is a cation,
n is an integer between 2 and 20.

7. A compound of the formula:

(5)

wherein R1 is selected from among —CH$_3$ and CH$_2$CH$_3$,
Cat$^+$ is a cation,
n is an integer between 2 and 20, and
R2 is a biomolecule.

8. A composition comprising an excipient and a compound that can activate a Tγ9δ2 lymphocyte, wherein said compound is selected from the group consisting of:
a) a compound of the formula:

(4)

wherein R1 is selected from among —CH$_3$ and —CH$_2$—CH$_3$,
Cat$^+$ is a cation,
n is an integer between 2 and 20; and
b) a compound of the formula:

(5)

according to claim 7.

9. The composition according to claim 8, further comprising a pharmaceutically acceptable excipient.

10. The composition according to claim 8, wherein said compound is diluted in a sterile phosphate buffer at pH 7.

11. The composition according to claim 8, wherein said composition is in the form of a composition that can be topically administered.

12. The composition according to claim 8, further comprising primate Tγ9δ2 lymphocytes.

13. The composition according to claim 8, further comprising a T lymphocyte growth factor.

14. A compound of the formula:

(5)

wherein R1 is selected from among —CH$_3$ and —CH$_2$—CH$_3$,
Cat$^+$ is a cation,
n is an integer between 2 and 20, and
R2 is selected from the group consisting of a nucleoside and a phosphoepoxide.

15. A composition comprising an excipient and a compound that can activate Tγ9δ2 lymphocytes, wherein said compound is selected from the group consisting of
a) a compound of the formula:

(4)

wherein R1 is selected from among —CH$_3$ and —CH$_2$CH$_3$,
Cat$^+$ is a cation, and
n is an integer between 2 and 20, and
b) a compound of the formula:

(5)

wherein R1 is selected from among —CH$_3$ and —CH$_2$CH$_3$,
Cat$^+$ is a cation, and
n is an integer between 2 and 20,
and R2 is selected from the group consisting of a nucleoside and a phosphoepoxide.

16. The method according to claim 1, wherein said compound is
a compound having a formula of:

(4)

wherein R1 is selected from among —CH$_3$ and —CH$_2$—CH$_3$,
Cat$^+$ is a cation, and
n is an integer between 2 and 20.

17. The method according to claim 1, wherein said compound is a compound having the following formula:

(5)

wherein R1 is selected from among —CH$_3$ and CH$_2$CH$_3$,
Cat$^+$ is a cation, and
n is an integer between 2 and 20, and
R2 is a biomolecule.

* * * * *

UNITED STATES PATENT AND TRADEMARK OFFICE
CERTIFICATE OF CORRECTION

PATENT NO. : 7,101,711 B1 Page 1 of 1
APPLICATION NO. : 09/786055
DATED : September 5, 2006
INVENTOR(S) : Christian Belmant et al.

It is certified that error appears in the above-identified patent and that said Letters Patent is hereby corrected as shown below:

Title page,
Item (57), Line 1: "de la Santa" should read --de la Sante--.

Column 3,
Line 59, "19,20-epoxy-1 g-methyl-1-eicosyl" should read
--19,20-epoxy-19-methyl-1-eicosyl--.

Column 7,
Line 33, should read

Column 24,
Line 36, "culture x-axis in Fig. 1)." should read --culture (x-axis in Fig. 1).--.

Signed and Sealed this

Twentieth Day of March, 2007

JON W. DUDAS
*Director of the United States Patent and Trademark Office*